US009383341B2

(12) United States Patent
Logan et al.

(10) Patent No.: US 9,383,341 B2
(45) Date of Patent: Jul. 5, 2016

(54) SONIC LUMBER TESTER

(71) Applicants: James D. Logan, Pullman, WA (US);
James R. Allen, Pullman, WA (US);
Harry E. Moore, Moscow, ID (US);
Dean A. Nelson, Pullman, WA (US);
Timothy T. Meekhof, Pullman, WA (US); Peter A. Siebold, Pullman, WA (US); Ryan D. Baldwin, Pullman, WA (US); Jean M. Logan, Pullman, WA (US)

(72) Inventors: James D. Logan, Pullman, WA (US);
James R. Allen, Pullman, WA (US);
Harry E. Moore, Moscow, ID (US);
Dean A. Nelson, Pullman, WA (US);
Timothy T. Meekhof, Pullman, WA (US); Peter A. Siebold, Pullman, WA (US); Ryan D. Baldwin, Pullman, WA (US); Jean M. Logan, Pullman, WA (US)

(73) Assignee: METRIGUARD INC., Pullman, WA (US)

( * ) Notice: Subject to any disclaimer, the term of this patent is extended or adjusted under 35 U.S.C. 154(b) by 0 days.

(21) Appl. No.: 14/066,504

(22) Filed: Oct. 29, 2013

(65) Prior Publication Data

US 2015/0247825 A1    Sep. 3, 2015

(51) Int. Cl.
*G01N 29/04* (2006.01)
*G01N 29/07* (2006.01)

(52) U.S. Cl.
CPC .............. *G01N 29/045* (2013.01); *G01N 29/07* (2013.01); *G01N 2291/0238* (2013.01); *G01N 2291/0258* (2013.01); *G01N 2291/02818* (2013.01); *G01N 2291/02827* (2013.01); *G01N 2291/044* (2013.01)

(58) Field of Classification Search
CPC .............. G01N 2291/0238; G01N 2291/0258; G01N 2291/02818; G01N 2291/02827; G01N 2291/044; G01N 29/045; G01N 29/07
USPC ........................................................ 73/12.09
See application file for complete search history.

(56) References Cited

U.S. PATENT DOCUMENTS 3,190,111 A    6/1965    Trussell et al.
3,196,672 A    7/1965    Keller (Continued)

OTHER PUBLICATIONS

Logan, James D., and Paul S. Kreager (1975) "Using a Microprocessor, A Resl-Life Application", Computer Design, Sep. 1975, P69-77, USA.

*Primary Examiner* — Hezron E Williams
*Assistant Examiner* — Gedeon M Kidanu

(57) ABSTRACT

The present invention is a wood grading apparatus including a robust "push" solenoid as a hammer means for impacting a lumber specimen under test. A conventional solenoid coil with stationary magnetic iron pole pieces is combined with a bimetallic armature including a magnetic portion and a nonmagnetic portion; said armature is of uniform cross section through the solenoid coil. A magnetic steel portion of said armature is fastened to a nonmagnetic steel portion thereof, whereby the magnetic field may act upon the magnetic portion of said armature and drive said nonmagnetic portion in an outward direction whereby impact or striking action is achieved. The present invention includes said solenoid in a wood grading apparatus whereby physical properties of wood are measured in a conveyor line setting and wood grading is affected by combining sonic velocity and density measurements to determine the modulus of elasticity of the wood object. Sonic velocity in the wood specimen is determined either by reverberation frequency or by rolling transducers that detect the leading edge of a stress wave initiated by said hammer means. A weight measurement means including a horizontal-axis roller lug conveyor chain and a leaf-spring suspension with a load cell means provides for improved accuracy in weight measurement for wood density calculation.

19 Claims, 10 Drawing Sheets

(56) References Cited

U.S. PATENT DOCUMENTS

| | | | |
|---|---|---|---|
| 3,531,690 A | 9/1970 | Pellerin | |
| 4,147,064 A | 4/1979 | Bond | |
| 4,201,093 A | 5/1980 | Logan | |
| 4,361,154 A | 11/1982 | Pratt, Jr. | |
| 4,852,029 A * | 7/1989 | Pope | G01N 3/20 209/521 |
| 5,024,091 A | 6/1991 | Pellerin et al. | |
| 5,237,870 A | 8/1993 | Fry et al. | |
| 5,396,799 A | 3/1995 | Ross et al. | |
| 5,503,024 A | 4/1996 | Bechtel et al. | |
| 5,621,172 A * | 4/1997 | Wilson | G01M 5/005 73/579 |
| 6,029,522 A | 2/2000 | Schafer et al. | |
| 6,347,542 B1 * | 2/2002 | Larsson | G01M 7/08 73/12.09 |
| 6,367,330 B1 | 4/2002 | Schafer | |
| 6,715,337 B2 | 4/2004 | Huang et al. | |
| 6,782,732 B2 * | 8/2004 | Huang | G01N 3/303 73/12.07 |
| 6,813,927 B1 * | 11/2004 | Harris | G01N 3/48 73/12.09 |
| 7,043,990 B2 * | 5/2006 | Wang | G01N 3/20 702/56 |
| 7,066,007 B2 * | 6/2006 | Ziegler | G01N 9/36 73/12.12 |
| 7,194,916 B2 * | 3/2007 | Ouellet | G01N 3/20 73/852 |
| 7,340,958 B2 | 3/2008 | Huang et al. | |
| 7,603,904 B2 * | 10/2009 | Harris | G01N 33/46 702/56 |
| 7,974,803 B2 | 7/2011 | Logan et al. | |
| 8,585,014 B2 * | 11/2013 | Oikawa | F16K 11/0716 251/129.15 |
| 2005/0086023 A1 * | 4/2005 | Ziegler | G01N 9/36 702/127 |
| 2008/0197054 A1 * | 8/2008 | Lindstrom | G01B 17/06 209/517 |
| 2010/0036633 A1 * | 2/2010 | Logan | G01N 33/46 702/85 |
| 2014/0292114 A1 * | 10/2014 | Bell | H02K 33/16 310/23 |

* cited by examiner

SONIC LUMBER TESTER

REFERENCES

U.S. Pat. No. 3,196,672 July 1965 Keller
Logan, James D., and Paul S. Kreager (1975) Using a Microprocessor, A Real-Life Application, COMPUTER DESIGN, September 1975
U.S. Pat. No. 4,201,093, Jul. 20, 1978, Logan
U.S. Pat. No. 4,926,350, May 15, 1990 Bechtel et al.
U.S. Pat. No. 5,237,870, Aug. 24, 1993 Fry et al.
U.S. Pat. No. 5,503,024 Apr. 2, 1996 Bechtel et al.
U.S. Pat. No. 7,066,007, Jun. 27, 2006 Ziegler, et al.
U.S. Pat. No. 7,194,916, Mar. 27, 2007, Ouellet, et al.
U.S. Pat. No. 7,340,958, Mar. 11, 2008 Huang, et al.
U.S. Pat. No. 7,603,904, Oct. 20, 2009 Harris, et al.
U.S. Pat. No. 7,974,803, Jul. 5, 2011 Logan, et al.

TECHNICAL FIELD

This invention relates to the field of electromechanical devices, more specifically the field of electromagnetic solenoid striking means whereby a mechanical action is effected as a result of causing an electric current to flow in a coil of conducting wire. For purposes of the present invention, the mechanical action is an impact. A further technical field is that of grading wood pieces for use in construction whereby physical properties are measured and/or predicted whereby efficient sorting of a variable wood resource provides groupings of material with more tightly controlled physical characteristics.

BACKGROUND OF THE INVENTION

In a lumber grading process one method of determining the modulus of elasticity E, (Young's modulus) of a lumber specimen is to strike a starting end of said lumber specimen to produce a compressive stress wave in the lumber specimen which travels to the opposite end thereof and reflects from the opposite end as a tensile wave. The tensile wave travels back to the starting end, where it reflects as a compression wave, thus producing an echo reverberation. A measurement of the frequency of reverberations provides a measurement of sonic velocity. Alternative detection means can be used to detect the progress of the original compression wave whereby sonic velocity is determined, so time domain measurement of the first compression wave is interchangeable with measurement of reverberation frequency. The sonic velocity value is then combined with measured lumber specimen density. The result is a measured E value that can be used in a sorting process to grade structural lumber for characteristics that are important in the design and serviceability of a wood structure. Making the sonic velocity measurement requires a means for producing a compression/tension sonic wave in the lumber specimen under test. Such means have included pneumatic cylinders, pendulum devices, manually operated hammers and electric solenoid actuated hammers. One solenoid actuated hammer device utilized a commercial solenoid attached to a sliding shaft means the hardened end of which impinged upon a steel clamping means which in turn was attached to the lumber specimen whereby the sonic energy from the impact of the sliding shaft means was transferred to the lumber specimen. This arrangement was suitable for stop-and-go laboratory conditions but did not lend itself to a production line situation in which the sonic energy must be transferred into a continuously moving specimen.

The present invention provides a simple robust means for impacting the end of a moving lumber specimen, such as a lumber specimen riding on a conveyor chain, for the purpose of sonic lumber grading.

DEFINITIONS

E—Young's modulus, or modulus of elasticity, typically expressed in units of pounds per square inch or Pascals (Newton/square meter). One pound per square inch equals 6894.76 Pascals This material property expresses the value of "stiffness" that is independent of shape.

I—Moment of inertia, typically expressed in units of $(inches)^4$, i.e., inches to the fourth power. For a rectangular cross section this is equal to (width times depth-cubed) all divided by 12. The depth dimension is the direction of applied bending load. Note that depth can be thickness or width of a lumber specimen depending upon the direction of applied load.

Dimension lumber—structural wood lumber shapes typically with a rectangular cross section and often 1-½ inch thick and 2-½ inch to 11-¼ inches wide in North America, also referred to as "timbers" in other countries with similar sizes expressed in metric units i.e., 35 mm to 45 mm thick by 70 to 300 mm wide. Metric sizes are typically actual cross section sizes whereas sizes in English units are smaller than the called-out sizes, thus leading to confusion until one gets the hang of it. This is a hold-over from history when lumber sizes were called out as the rough green size, and were smaller after drying shrinkage and surfacing. Now this is no longer true because the actual rough green sizes have been reduced by better understanding of drying shrinkage, improved precision in cutting and reduction of clean-up in the surfacing operation. What we know as a "two-by-four" is actually 1-½ by 3-½ inches in cross section.

Boards—wood used for general applications typically with a rectangular cross section and thicknesses reckoned in quarters of an inch and widths ranging from 2-½ inch to 11-¼ inch. Again, actual sizes are smaller than the call-out size, so a "one-by-four" is ¾ inch by 3-½ inches.

Timber—In the US and Canada this term typically refers to wood in rectangular cross sections larger than 1-½" thick, but in other countries this term can refer to dimension lumber cross sections as well.

Lumber specimen—for purposes of this invention, this term includes dimension lumber, boards and timbers. Lengths may range from less than 6 feet to more than 20 feet.

DETAILED DESCRIPTION OF THE PREFERRED EMBODIMENT

Figure 1:
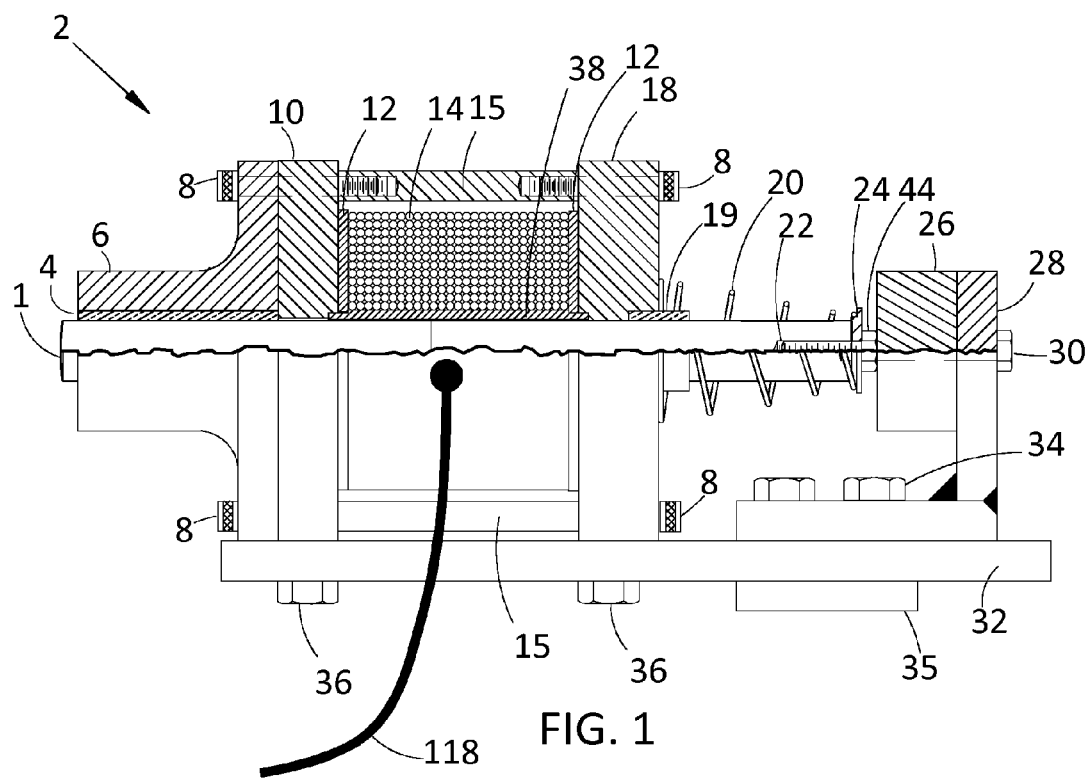
FIG. 1 is a side elevation view of the electric hammer portion of the present invention showing cut-away sections exposing an armature, a first bearing, a bearing mount, a coil and a first and a second pole pieces of a magnetic circuit, a second bearing, a spring and a bumper.

One object of the present invention is to provide a hammer means with robust construction to impinge upon the ends of a lumber specimen whereby impulsive sound waves are caused to travel through the length of said lumber specimen and measurements of physical properties may be derived from sound velocity and/or reverberation frequency.

Another object of the present invention is to provide a hammer means with a low wear rate whereby many millions of impacts may be applied with minimal service requirements.

Another object of the present invention is to provide a hammer means that will avoid the problems of dirt, moisture and variable air pressure found in pneumatically operated hammer means.

Another object of the present invention is to minimize the number of and fragile nature of moving parts typically found in pneumatically driven hammer means.

Another object of the present invention is to provide for lumber grading in material with sufficient detail within each lumber specimen that trim decisions may be based on wood properties within potential trim segments of each lumber specimen rather than based only on average properties.

Another object of the present invention is to include improved hammer means in a wood grading system that measures average wood properties by determining sonic reverberation frequency.

FEATURES AND ADVANTAGES OF THE PRESENT INVENTION WITH COMPARISON TO THE PRIOR ART

Prior art pneumatic hammer devices contain many moving parts all subject to failure, and subject to damage from contamination in the air supply which is always a problem in the production line setting. When a pneumatic cylinder is used in an application requiring rapid cycling over a long period of time, problems arise with both internal and external seals which have a limited lifetime. When such a device is used in an impacting or hammer application, additional problems arise from shock loading of the internal components.

Arrangements of equipment utilizing reverberation frequency as an indicator of sonic velocity do not provide detail that would be more useful in making structural assessments of a lumber specimen, whereas the rolling transducer features of this invention can provide that detail. In a preferred alternative embodiment of the present invention, sonic velocity is measured over incremental distances along the lumber specimen whereby portions of the specimen with low strength and stiffness properties may be identified and eliminated by trimming.

THE PRESENT INVENTION

The present invention includes a robust hammer with essentially one moving part plus one spring and including a rotational break-away feature whereby damage to the hammer assembly is avoided in the event of a spring failure or entanglement with lumber specimens in the production line. There are no internal or external seals to wear out. The present invention can be arranged to use sonic reverberation frequency as an indicator of average wood properties in a specimen or by use of rolling transducers, internal detail may be measured to better make grade and trim decisions for each lumber specimen. The present invention electric hammer is capable of many millions of hammer blows between maintenance events and is capable of high speed operation up to and exceeding 250 strikes per minute.

One preferred embodiment of the present invention is a push-type electrical solenoid assembly 2 shown in FIG. 1 having an armature 1 slidably supported by a first bearing 4 in a bearing mount 6, a first pole piece 10, side pole pieces 15, a second pole piece 18, a second bearing 19, a return spring 20, a spring retainer 24, a bumper 26, a bumper mounting means 28, bolt means 30 for connecting bumper 26 with bumper mount means 28, a bobbin means consisting of coil bobbin end means 12 and coil bobbin core means 38, coil 14 of insulated conducting wire wound on bobbin means and assembled using bolt means 8, and mounted to a base plate 32 by fastening means 36. Said bumper 26 is preferably made of an energy absorbent rubber such as polyurethane. Said bumper mounting means 28 fastened to base plate means 32 by fastening means 34 and tapped retainer means 35. Pole pieces 10, 15, and 18 constructed of magnetic iron the ferromagnetic properties of which provide for concentration of magnetic field inside coil bobbin means 38. Electrical solenoid assembly coil 14 is connected to solenoid drive circuit shown in FIG. 4 through electrical cable 118. Said assembly 2 forming an electric hammer for the present invention.

Figure 2:
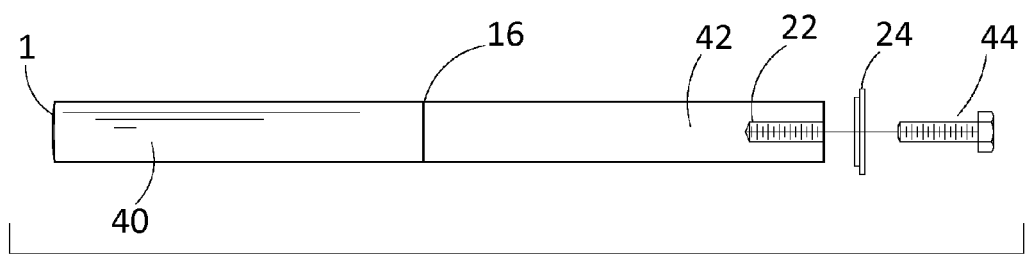
FIG. 2 is a side view of the armature with spring retainer and a bolt.

Armature means 1 shown in FIG. 2 includes a first portion 42 composed of a magnetic material such as 1018 grade steel, and a second portion 40 composed of a nonmagnetic material such as grade 304 stainless steel, the two portions 40 and 42 fastened together by welding means 16. Said magnetic portion 42 drilled and tapped 22 to receive a bolt means 44, whereby spring retainer 24 is held in place. Spring retainer means 24 is preferably contoured whereby spring means 20 is maintained concentric with armature 1.

Figure 3:
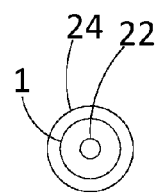
FIG. 3 is an end view of the armature.

FIG. 3 shows an end view of armature means 1 with spring retainer 24 and showing the location of drilled and tapped hole 22.

In operation, upon energizing coil 14 a magnetic field is produced that pulls the ferromagnetic portion 42 of armature 1 into the magnetic field flux thereby moving the nonmagnetic portion of the armature in an outwardly directed motion through bearing 4, and compressing return spring 20. Said outwardly directed motion is sustained until armature 1 encounters a target material or the magnetic forces and inertial effects are balanced by the force exerted by return spring 20, and until coil 14 is de-energized. Upon de-energizing coil 14, armature 1 is accelerated in the inward direction by spring 20 until bolt means 44 encounters bumper means 26, at which time armature 1 comes to a stop.

Figure 8:
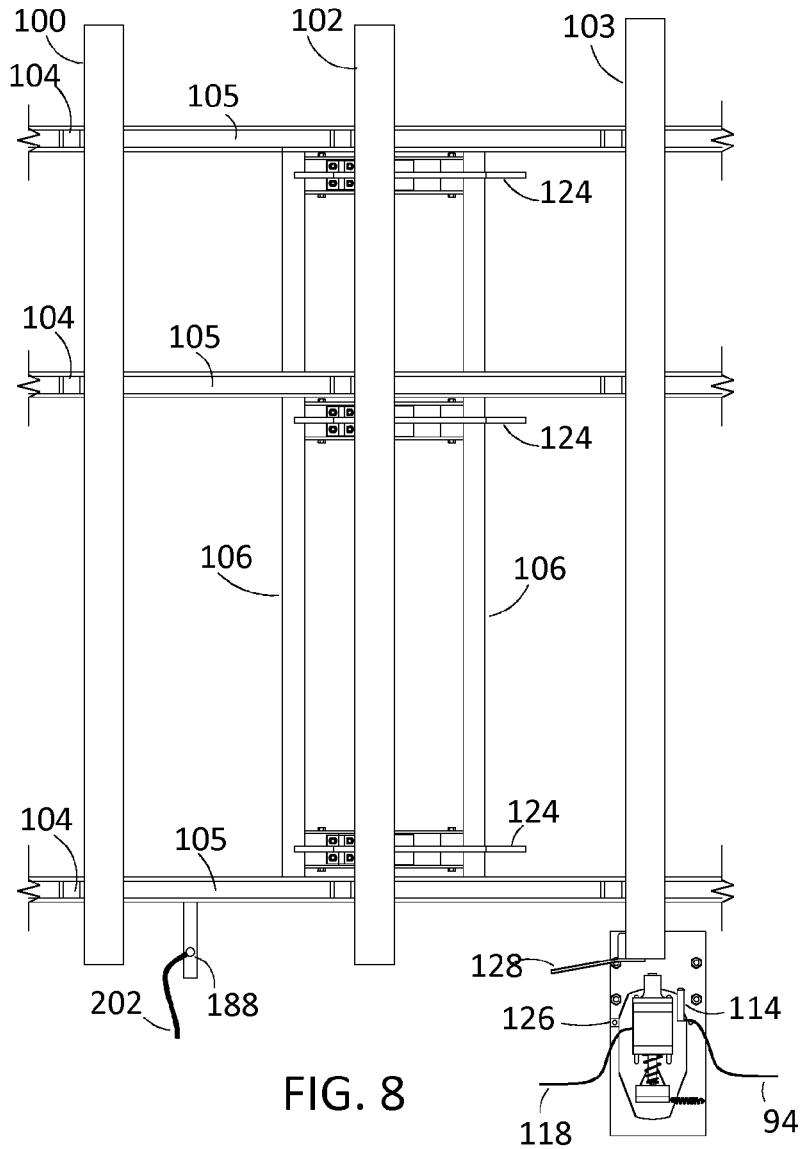
FIG. 8 is a plan view of a chain conveyor means with a multiplicity of weight measurement means, electric hammer assembly, photo sensor means, shaft encoder means and acoustic sensor means operatively arranged for sonic grading of lumber specimens.

For maximum impact force coil 14 continues to be energized while armature 1 is moving toward an impact target, and then de-energized at the instant of impact, allowing rebound and spring forces to return armature 1 to its starting position. If impact energy is desired to be reduced, a shorter energized time is selected. The impact target in the case of a lumber testing application is an end of a lumber specimen 103 such as shown in FIG. 8.

Maximum impact velocity is achieved when the starting position of armature 1 is adjusted so impact occurs before return spring 20 begins to slow the outward progress of armature 1.

Figure 4:
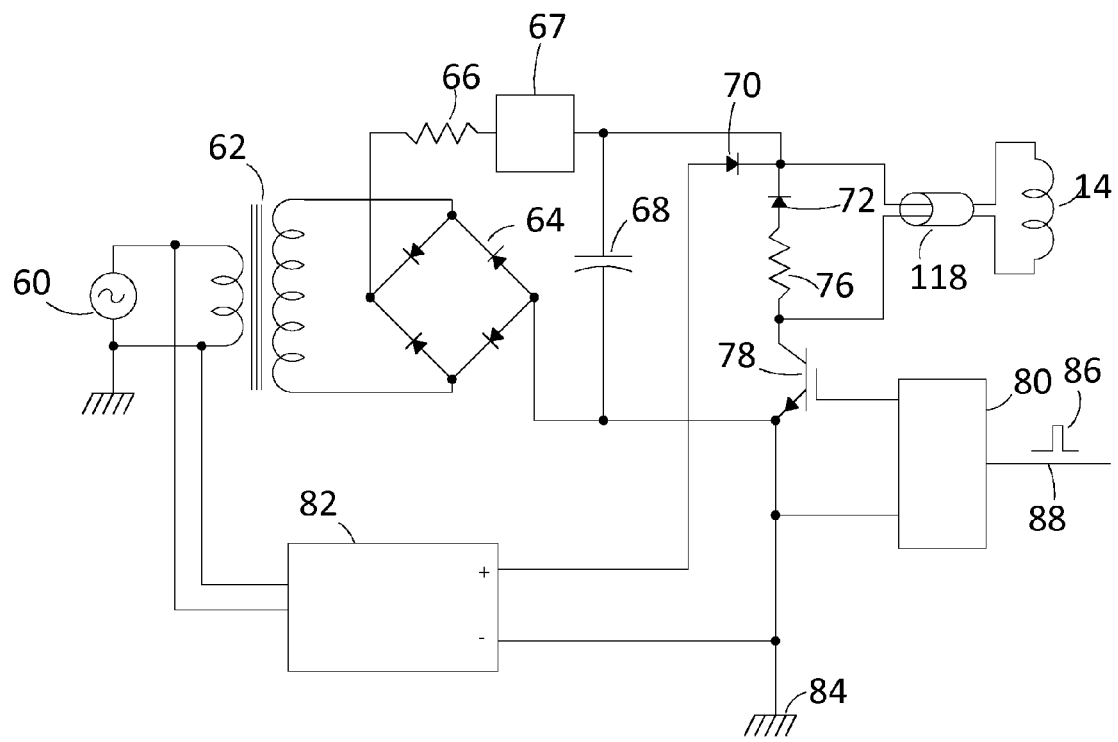
FIG. 4 is a schematic wiring diagram of a solenoid driver circuit.

Electrical drive to coil 14 is provided in a preferred embodiment by means of the circuit shown in FIG. 4. A source of electrical power 60 is connected through appropriate switch gear (not shown) to the primary winding of transformer 62 and dc power supply 82. The secondary winding of transformer 62 is connected to a full-wave bridge rectifier means 64. The positive side of rectifier bridge 64 is connected through a resistor 66 and intermittently through charge control switch means 67 to a first side of an energy storage capacitor 68, the negative side of rectifier bridge 64 is connected to a second terminal of energy storage capacitor 68 and grounding connection 84. Said energy storage capacitor 68 is connected through cable 118 to a first winding connection of solenoid coil 14. A second winding connection of solenoid coil 14 is connected through cable 118 to the collector of an Insulated Gate Bipolar Transistor (IGBT) 78, and to an energy dissipating resistor 76.

A high-speed, high current Schottky diode 72 directs coil fly-back energy to the first winding connection of solenoid coil 14. Resistor 76 and diode 72 suppress high voltages that occur when current in an inductor such as solenoid coil 14 is interrupted. In one preferred embodiment, the first winding connection of solenoid coil 14 is also supplied current from a dc power supply 82 through diode 70 while IGBT 78 is in the "ON" state and after the voltage across energy storage capacitor 68 is decreased to a value slightly below the output voltage of power supply 82. The combination of high and low voltage power supplies and switching network of FIG. 4 provide for rapid increase of current in solenoid coil 14 from the instant IGBT 78 is turned "ON", which current is sustained until IGBT 78 is turned "OFF". A logical input control signal 86 on input connection 88 is fed to integrated gate driver circuit 80 to provide appropriate control to the gate of IGBT 78 for rapid switching. The combination of voltage and current supplied to solenoid coil 14 greatly reduces the response time of the solenoid while limiting peak current to a workable level whereby quick response from the electric hammer is achieved. In a second preferred embodiment power supply 82 is not used, and the electrical energy is supplied by capacitor 68.

Figure 5:
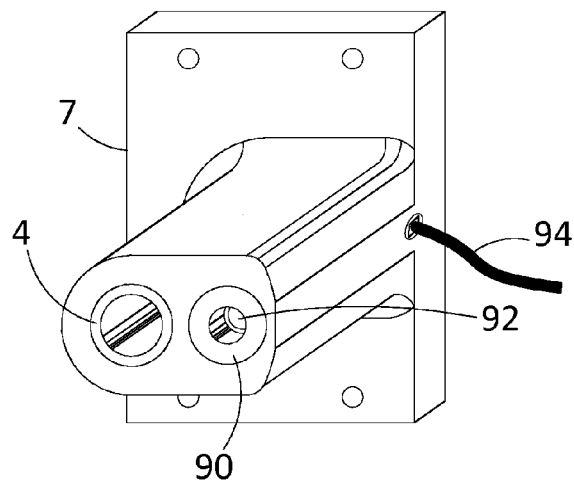
FIG. 5 is an isometric view of an alternative bearing part with acoustic sensor means included.
Figure 14:
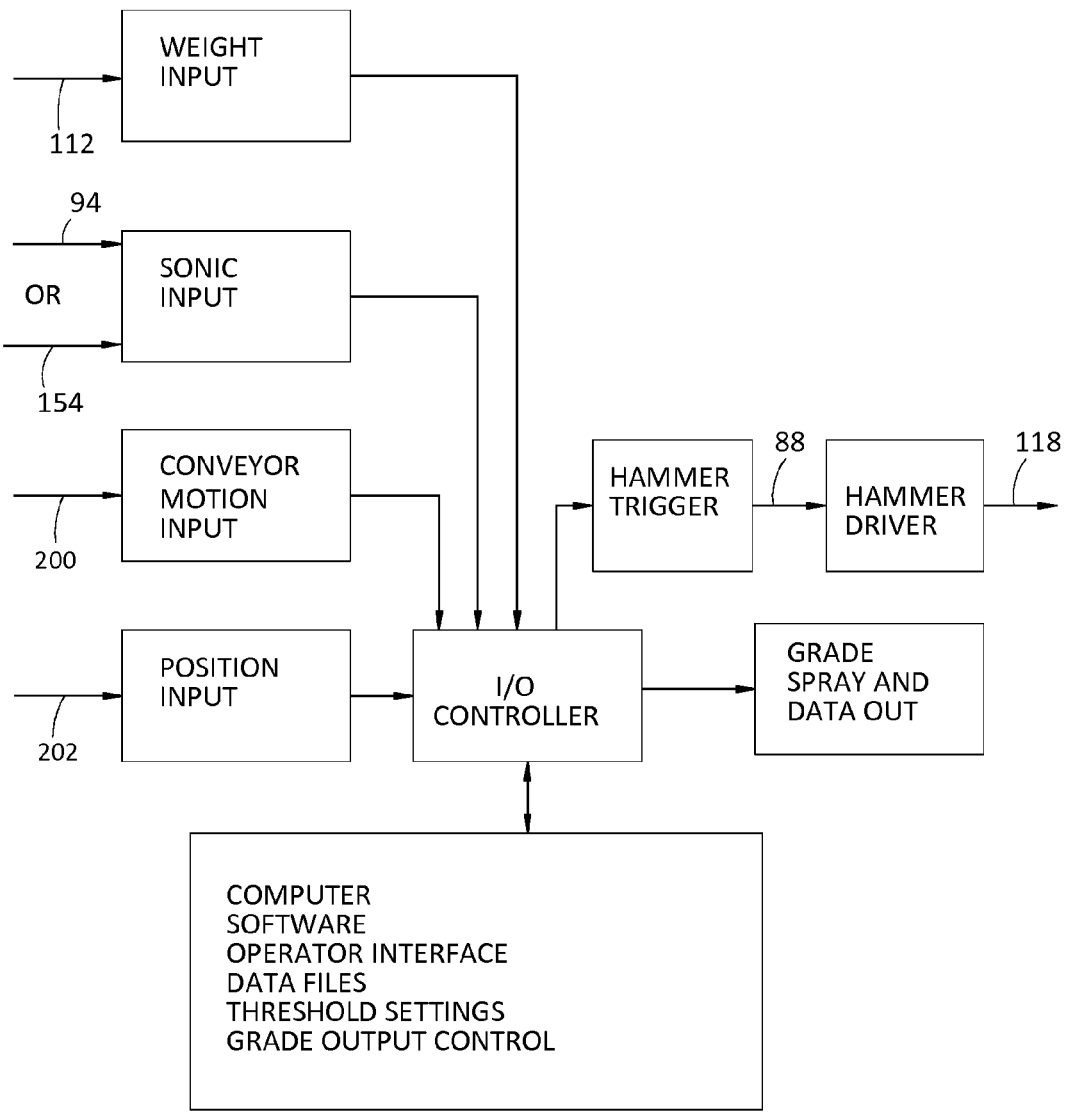
FIG. 14 is a block diagram illustrating information flow in an electronic means for a grading apparatus of the present invention.

Referring to FIG. 5, for sonic lumber grading, impact energy imparted to the end of a lumber specimen induces a reverberating sound wave the fundamental frequency of which is detected by means of acoustic sensor 92 mounted in sound dampening means 90 and enclosed in alternative solenoid front bearing mount 7 and connected through shielded cable means 94 to electronic means further described in FIG. 14. Alternatively a sonic detection means such as a microphone or array of acoustic sensors may be mounted external to electrical solenoid assembly 2 whereby reverberation energy from the end of the lumber specimens is detected and the frequency thereof measured.

Figure 6:
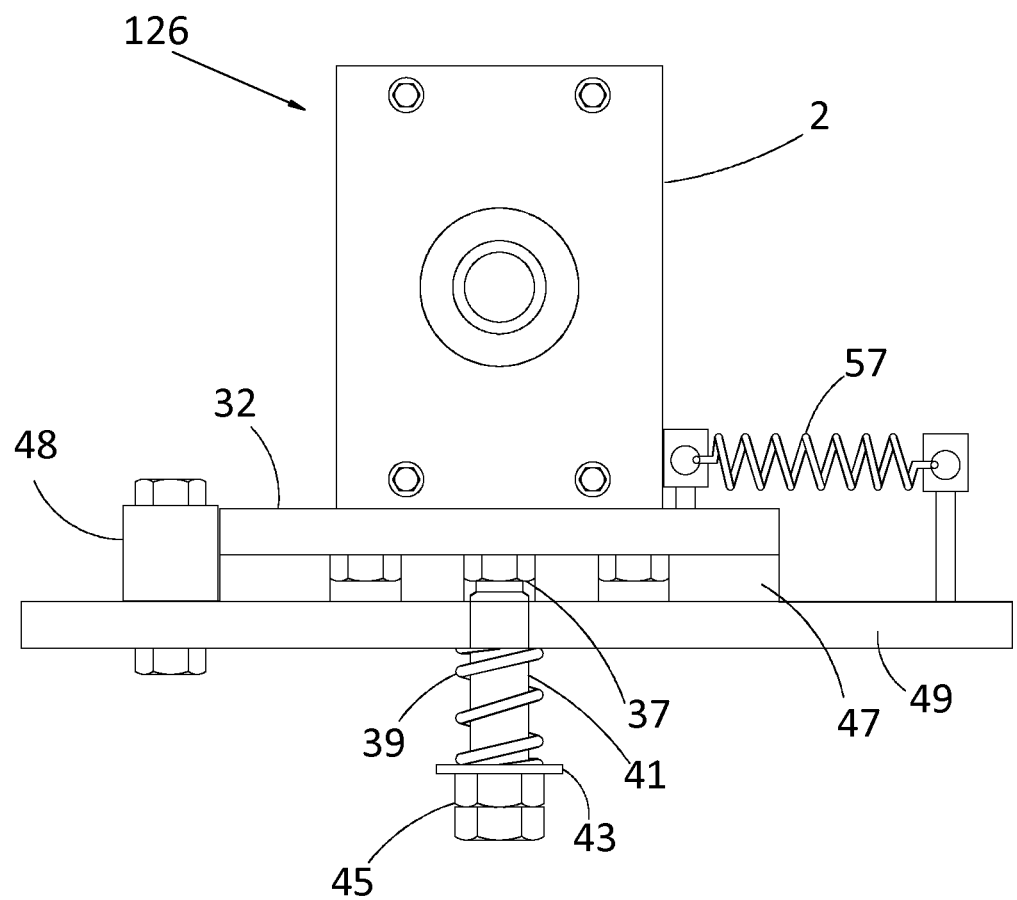
FIG. 6 is an end view of an electric hammer assembly pivotably mounted on a fixed base plate.

An electric hammer assembly 126 is shown in FIG. 6. The end view of electrical solenoid assembly 2 is shown in FIG. 6 pivotably mounted on base plate 49 with bolt 41, lock nut 37 spring 39 washer 43 and jam nuts 45. A slide-bearing plate 47 preferably made of UHMW polyethylene or other suitable material rotates against lower mounting plate 49 for rotational movement about a vertical axis at the center of bolt 41. The upper end of bolt 41 is threaded into the upper mounting plate 32 of electrical solenoid assembly 2 and locked in place by means of lock nut 37. It is recognized that spring 39 may take the form of an alternative wave washer or stacked lock washers if it is desirable to reduce the vertical length of the assembly. Rotational stop 48 and spring 57 allow freedom of rotational motion about bolt 41 in case of a fault in electrical solenoid assembly 2 that leaves it exposed to interference with lumber on lug chain conveyor described elsewhere, and provides for return to a normal operating position after such encounter.

Figure 7:
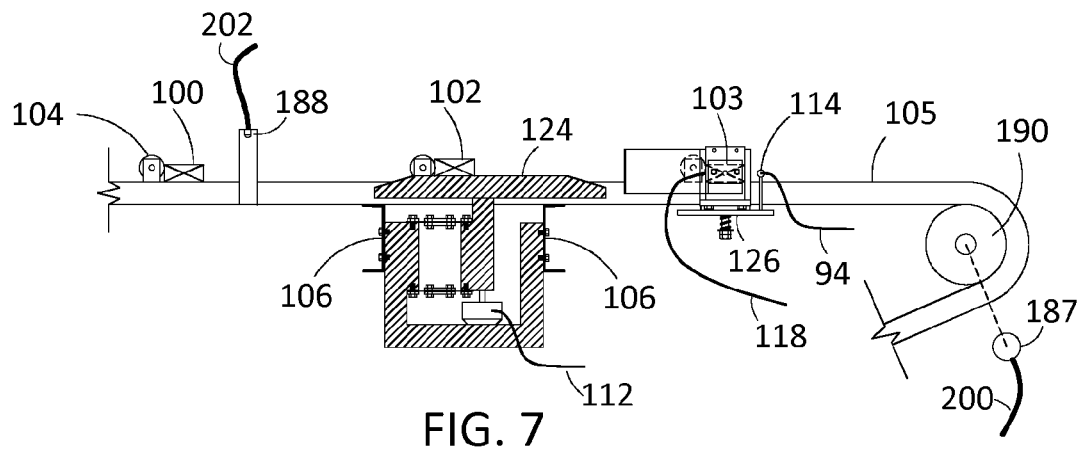
FIG. 7 is an elevation view showing a section of a chain conveyor means with a weight measurement means, an electric hammer assembly and acoustic sensor means operatively arranged for sonic grading of dimension lumber.

FIG. 7 shows an elevation view of a section of chain conveyor means with sequence of lugs 104 transporting lumber specimens 100, 102 and 103 over weight measurement means 124 and adjacent electric hammer assembly 126. Each weight measurement assembly 124 is connected to weight input of FIG. 14 by cable 112. An alternative mounting of acoustic sensor means 114 is shown adjacent electric hammer assembly 126 with acoustic sensor means 114 in juxtaposition with the end of lumber specimen 103 (hidden) whereby sonic reverberation energy is detected from lumber specimen 103 after impact by electrical solenoid assembly 2. Acoustic sensor means 114 is connected to sonic input of electronic means of FIG. 14 by cable 94. Conveyor chain 105 is driven by a sprocket shown schematically as 190. A rotary shaft encoder 187 connects to conveyor motion input of electronic means of FIG. 14 by cable 200 whereby position information is provided to electronic means for timing purposes. A photo sensor 188 connects through a cable 202 to electronic means of FIG. 14 whereby the presence or absence of a lumber specimen on the conveyor chain and position information is available through shaft encoder 187 so the weight measurement process start and stop is affected and so electrical solenoid assembly 2 may be fired to hit the approximate horizontal center of an end of lumber specimen 103.

Figure 13:
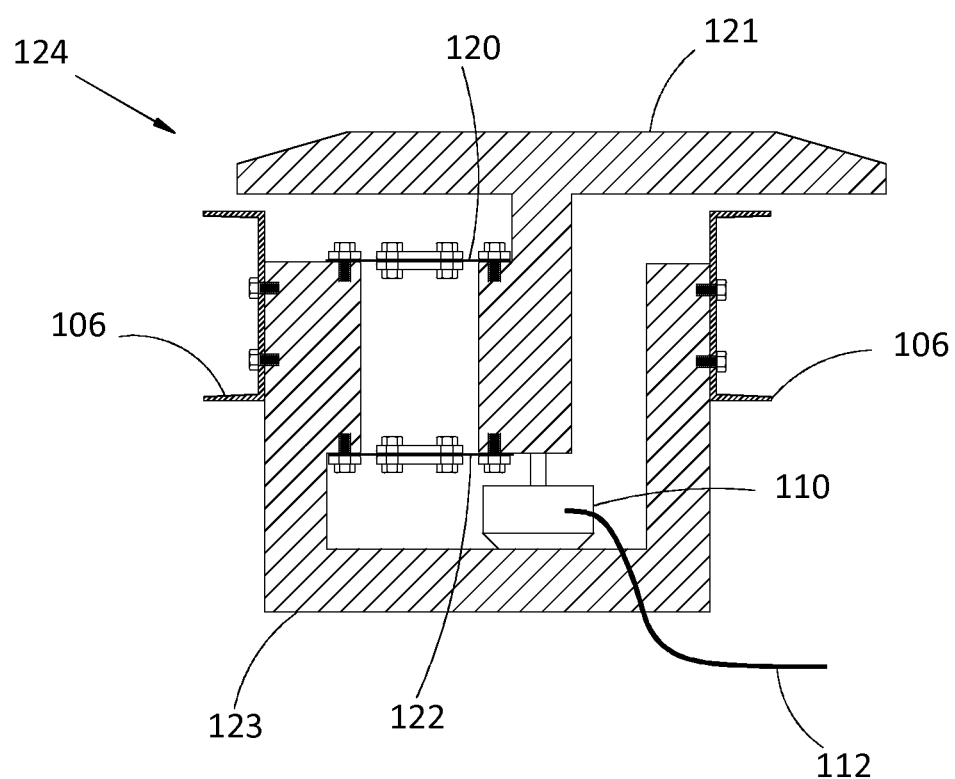
FIG. 13 is a vertical cross section of a weight measurement assembly.

A multiplicity of weight measurement assembly 124 can be supported from the conveyor flight structure by mounting means 106 composed of C-channel in the preferred embodiment shown in FIG. 13.

A weight measurement assembly 124 is shown in vertical cross section in FIG. 13. Linkages 120 and 122 are composed of spring steel pieces clamped by bolts to frame member means 123. Scale platform means 121 is suspended by linkages 120 and 122 in an arrangement that isolates load cell 110 from off-axis loads and makes weight determination independent of the horizontal placement of lumber specimen on scale platform means 121. Load cell 110 is connected to operative electronics means shown in FIG. 14 through cable 112. Means are provided (not shown) for vertical adjustment of weight measurement assembly 124 with respect to mounting means 106 at a preferred elevation with respect to conveyor chains. The weight measurement assembly may be supported either directly from conveyor chain support structure or from building components.

As shown in FIG. 8, a multiplicity of conveyor chains 105 may be fitted with weight measurement means 124. Shear plate means 128 is used to position lumber specimen 103 at a preferred distance from electrical solenoid assembly 2 whereby electrical solenoid assembly 2 may deliver a single impact smartly to the end of lumber specimen 103 and thereby produce a useful reverberation of sonic energy within the lumber specimen, which reverberation produces sonic emanations from the end of lumber specimen 103 as a sound wave, which in turn is converted by acoustic sensor 114 into an electrical signal and operatively connected to sonic input of electronic means of FIG. 14 through cable 94.

Figure 9:
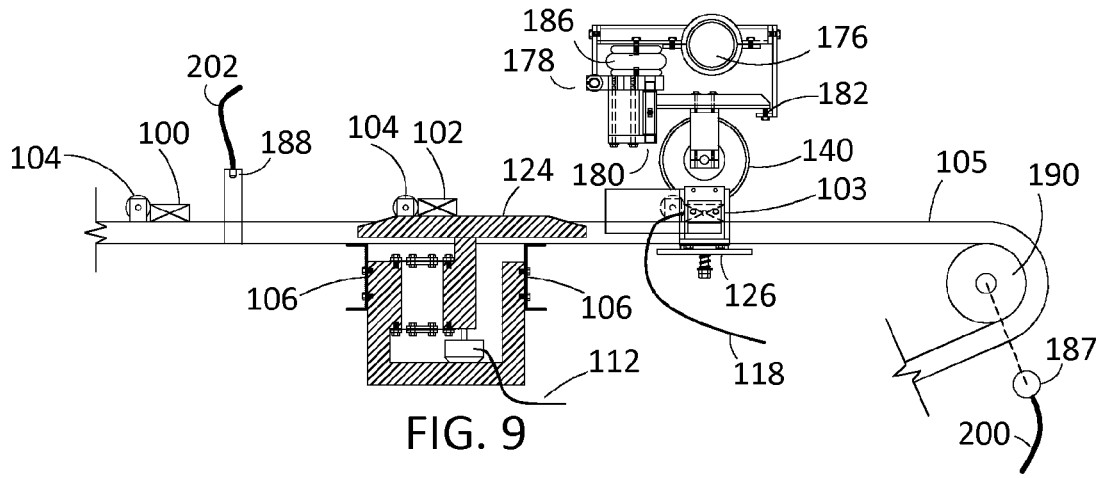
FIG. 9 is an elevation view showing a section of chain conveyor means with weight measurement means, photo sensor means, shaft encoder means, electric hammer assembly and rolling transducer means.
Figure 10:
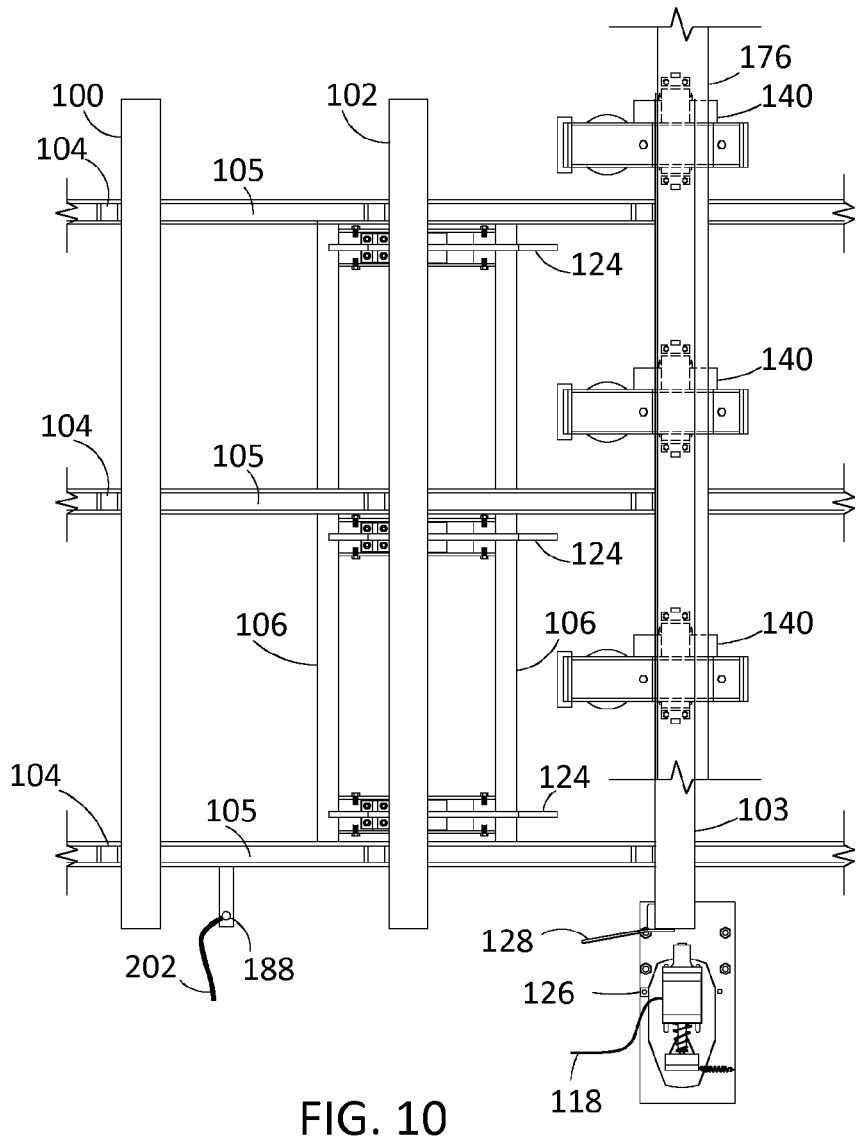
FIG. 10 is a plan view of a chain conveyor means with a multiplicity of weight measurement means, photo sensor means, and electric hammer assembly and a multiplicity of rolling transducer means operatively arranged for sonic grading of lumber specimens.

An alternative preferred embodiment of the present invention is shown in FIG. 9 and FIG. 10. In this alternative preferred embodiment, sonic energy is detected by a multiplicity of rolling transducer assemblies 140 arranged to contact lumber specimen 103 at preferred distances along the length of lumber specimen 103. With this alternative preferred embodiment the sonic wave leading edge is detected during the first transit of compressive wave energy emanating from a hammer impact produced by electrical solenoid assembly 2 on an end of said lumber specimen. This provides an advantage of obtaining localized sonic velocity and thus localized property information along the length of the lumber specimen, and the capability of measuring lumber specimens in which sonic wave attenuation prohibits measurement of reverberation frequency.

A location photo sensor 188 with signal cable 202 and shaft encoder 187 with signal cable 200 as described above are used in the alternative preferred embodiment shown in FIG. 9 and FIG. 10 whereby each lumber specimen may be tracked as to its location as it proceeds along the conveyor. As shown in FIG. 9, a typical rolling transducer assembly 140 is suspended above the chain conveyor by a bridge means 176 to which is fastened a transducer mounting means including an air spring 186, a first pivot bearing 178 whereby the wheel assembly may move in a vertical direction, a second bearing means 180 whereby the rolling transducer assembly 140 may swing through a limited angle about a vertical axis and automatically track the moving specimen 103 without skidding thereupon. The air spring 186 provides for an adjustable contact force between rolling transducer assembly 140 and lumber specimen 103. A stop bolt and lock nut 182 provide for parking the rolling transducer assembly 140 at a preferred distance above the conveyor chain 105 to affect suitable contact force for detection of stress waves in the lumber specimen and reducing bouncing and vertical motion to a manageable value. Bridge means 176 may be a round steel tube as shown or it may another cross section shape such as a square or rectangular tube or truss capable of spanning the required distance while minimizing deflection from varying loads and providing convenient fastening of transducer mounting means. Conveyor chain 105 with lugs 104 carries lumber specimens shown as 100, 102 and 103 in sequence first under photo sensor means 188, over weight measurement assemblies 124, and into the sonic velocity measurement position where lumber specimen 103 is impacted by electrical solenoid assembly 2 while in contact with rolling transducer assemblies 140. Movement of conveyor chain 105 is detected by shaft encoder 187 shown in FIG. 9 which is connected to conveyor motion input shown in FIG. 14 by cable 200. By these features, the start and stop times of weight measurement for lumber specimen 102 is determined, signals from weight measurement assemblies 124 on cables 112 are properly processed by electronic means and the hammer firing time for hammer assembly 126 is known so that lumber specimen 103 is in proper position for measurement of sonic velocity along the segments described by rolling transducer assemblies 140.

FIG. 10 shows the relative locations of lumber specimens 100, 102 and 103 as they move in sequence past photo sensor 188, weight measurement assembly 124 and hammer assembly 126.

Figure 11:
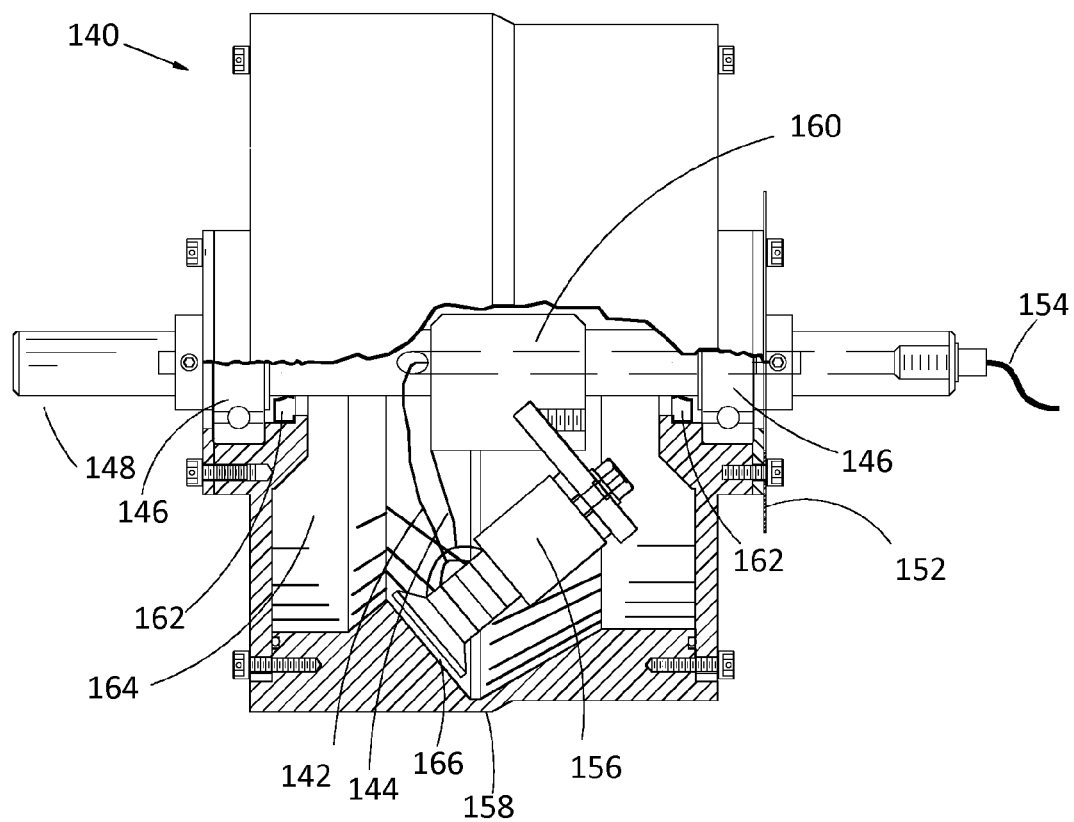
FIG. 11 is a cut-away view of rolling transducer means.

Rolling transducer assembly 140 shown in FIG. 11 includes a piezoelectric detection means 156 attached to a mounting means 160. Shaft 148 includes a longitudinal passage for electrical connection 142 leading to external cable 154 through a suitable connector. A grounding wire 144 provides zero potential reference for piezoelectric detection means 156 by connecting through mounting means 160 to non-rotating shaft 148. Bearings 146 and seals 162 allow for rotation of outer shell 158 about shaft 148. A coupling fluid such as oil fills the internal space 164 and couples sonic energy entering shell 158 to piezoelectric detection means 156 through running gap 166 between shell 158 and piezoelectric detection means 156. A grounding ring 152 provides for static electricity discharge through a carbon fiber brush not shown.

Figure 12:
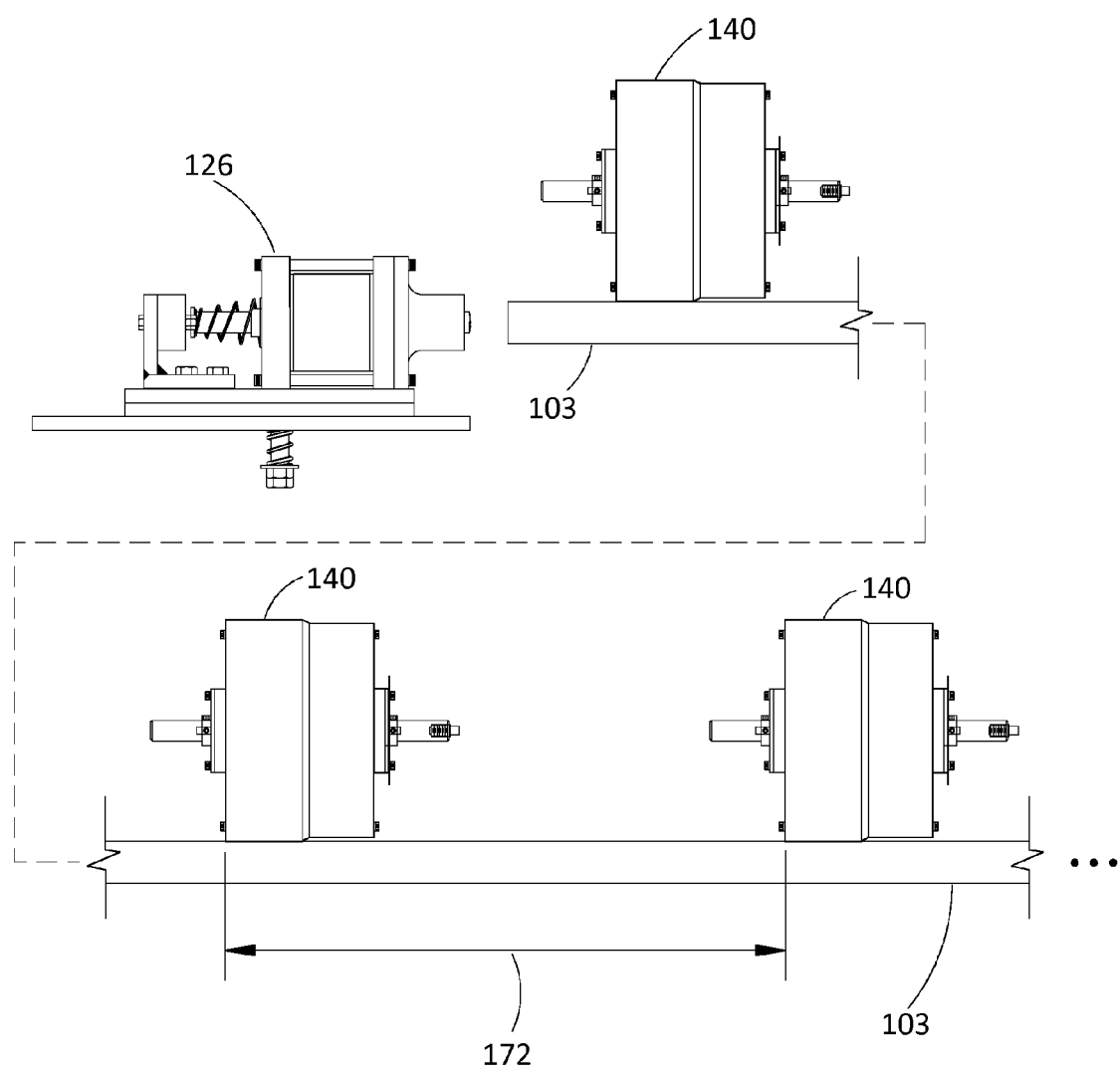
FIG. 12 is a schematic elevation view of electric hammer assembly arranged with a lumber specimen under test and in contact with a multiplicity of rolling transducer means.

FIG. 12 shows an arrangement of electric hammer assembly 126 arranged to strike the end of lumber specimen 103 which is in contact with rolling transducer assemblies 140 spaced apart by a preferred distance 172. Said preferred distance 172 may be chosen to coincide with typical lumber trim cutting distances so that trim decisions may be made based on the wood properties within a preferred trim increment.

In operation the weight of a lumber specimen under test is determined by the weight measurement means. A stress wave is initiated by electric hammer assembly 126. The stress wave moves along the lumber specimen at a sonic velocity and is detected as it proceeds along the lumber specimen by rolling transducer assemblies 140. The velocity is measured and the E is calculated for each increment of lumber between preferred distances 172. Although the figures and descriptions indicated that weight is first determined then sonic velocity is determined, these steps may be carried out in opposite order.

FIG. 14 shows a block diagram including the elements of the data processing system, whereby signals conducted by cables 112 from the weight measurement means, signal on cable 94 from the acoustic sensor or alternatively signals conducted by cables 154 from the rolling transducer means, signals conducted by cable 200 from the shaft encoder 187, and a signal from photo sensor 188 for position input conducted by cable 202 are combined and processed. A hammer drive trigger signal 88 is derived from the conveyor motion input and the position input and a hammer drive impulse is conducted by cable 118 to coil 14. Data from computations carried out in computer software may be supplied in the form of a grade spray control output or digital data output to network connections for use in downstream equipment.

Figure 15:
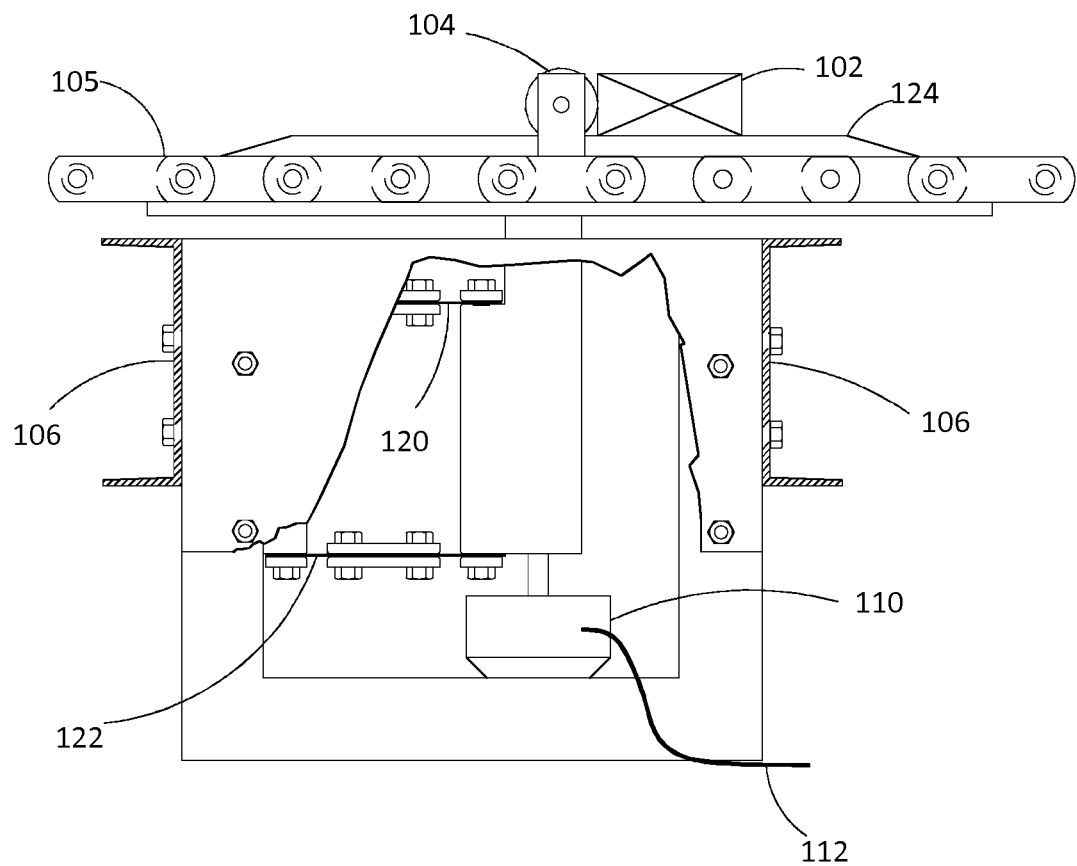
FIG. 15 is a vertical cross section of a chain conveyor with a horizontal axis roller lug carrying a lumber specimen under test over a weight measurement means with cut-away showing spring mounting means to reconcile vertical forces to a load cell.

FIG. 15 illustrates a conveyor chain 105 with horizontal axis roller lug 104 pushing a lumber specimen 102 over a weight measurement assembly 124 which is supported by mounting means 106. Mounting means 106 may be supported by chain conveyor flight not shown or from other support structures to avoid vibration motion being conducted to the load cell 110. The lumber specimen under test 102 rests on a slide arrangement, the vertical force therefrom is directed to a load cell 110. Springs 120 and 122 support horizontal forces only, so all the weight force is directed to the load cell 110 while lumber specimen 102 is in contact with slide arrangement 121. As lumber specimen under test 102 moves across weight measurement assembly 124 moment forces are resolved into tensile and compression forces in springs 120 and 122 whereby the force applied to load cell 110 does not change as a function of position along the top of weight measurement assembly 124.

Figure 16:
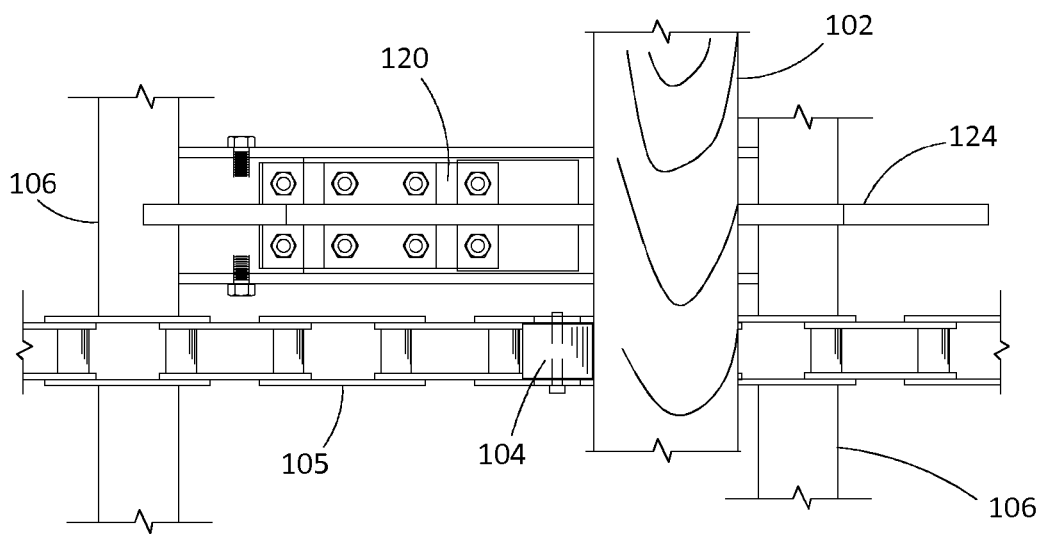
FIG. 16 is a plan view of a chain conveyor means with horizontal axis roller lug pushing a lumber specimen under test over a weight measurement assembly.

FIG. 16 is a plan view showing conveyor chain 105 with horizontal axis roller lug 104 pushing lumber specimen 102 across weight measurement assembly 124. For clarity the support conveyor flight for chain 105 has been removed. Horizontal axis roller lug 104 provides motive force to convey lumber specimen 102 across weight measurement assembly 124 whereby vertical force arising from friction of contact between the roller lug 104 and lumber specimen 102 is reduce to a minimum value. By using this method of conveyance the accuracy of weight measurement is improved.

In compliance with the statute, the invention has been described in language more or less specific as to structural features. It is to be understood, however, that the invention is not limited to the specified features shown, because the means and construction herein disclosed comprise a preferred form of putting the invention into effect. The invention is, therefore, claimed in any of its forms or modifications within the proper scope of the appended claims appropriately interpreted in accordance with the doctrine of equivalents.

The invention claimed is:

1. An apparatus for grading a wood lumber specimen including an electric hammer with a bimetallic armature for striking a first end of said wood lumber specimen, and an acoustic sensor means for detection of sonic reverberation in said wood lumber specimen and a computer processing means whereby said wood lumber specimen is struck on the first end of the wood lumber specimen by the bimetallic armature thereby inducing a sonic reverberation in the wood lumber specimen, and a property information value is calculated for the wood lumber specimen from the wood lumber specimen density and the sonic reverberation in the wood lumber specimen: and, the electric hammer includes a solenoid coil wound with electrically conductive wire and a cylindrical open center extending from a first end of the solenoid coil to a second end of the solenoid coil; and, a magnetic circuit means composed of ferromagnetic material whereby a magnetic field is conducted externally around the solenoid coil; and, a first linear bearing means arranged at the first end of the solenoid coil such that the first linear bearing means is maintained in coaxial alignment with the cylindrical open center of the solenoid coil; and, a second linear bearing means arranged at the second end of the solenoid coil such that the second linear bearing means is maintained in coaxial alignment with the cylindrical open center of the solenoid coil: and, the bimetallic armature is composed of a magnetic steel portion and a nonmagnetic steel portion with a transition there-between and with constant circular cross section of a diameter that provides a loose running fit between the bimetallic armature and the first and the second linear bearing means and the cylindrical open center of the solenoid coil, the first and the second linear bearing means allowing axial movement of the bimetallic armature: and, the magnetic circuit means and the bimetallic armature do not include an operative air gap; and, a return spring whereby the bimetallic armature is urged into a preferred starting position when said solenoid coil is not conducting electric current: and, a stop-bumper means arranged adjacent to the second linear bearing means to set the position of the preferred starting position: and, an electric circuit means for supplying an electric current impulse to the solenoid coil whereby the electrical current impulse causes the magnetic field to be generated in the solenoid coil and the bimetallic armature is caused to accelerate rapidly in a direction that extends the bimetallic armature outwardly and away from the stop-bumper to a preferred distance at which point it strikes the first end of the wood lumber specimen with a single impact thereby producing a compressive stress wave and sonic reverberation in said wood lumber specimen and the wood lumber specimen density is determined in any conventional manner.

2. The apparatus of claim 1 in which the bimetallic armature is fully engaged in the first and the second linear bearing means throughout a preferred operating cycle including rest against the stop-bumper means in the preferred starting position, acceleration away from the stop-bumper means and towards the first linear bearing means, impact against the first end of the wood lumber specimen, and return to the preferred starting position.

3. The apparatus of claim 1 in which the magnetic steel portion of the bimetallic armature is 1018 steel alloy and the nonmagnetic steel portion is stainless steel alloy 304.

4. The apparatus of claim 1 in which a connection between the magnetic steel portion and the nonmagnetic steel portion of the bimetallic armature is made by a welding process.

5. The apparatus of claim 1 in which the transition between the magnetic steel portion and the nonmagnetic steel portion of the bimetallic armature is positioned between the first and the second ends of the solenoid coil at a preferred location near a mid-point of the solenoid coil when the solenoid coil in a non-energized condition.

6. The apparatus of claim 1 in which the electric circuit means comprises an energy storage capacitor means, an electrical charging means, and an electronic switch means whereby electrical energy stored in the energy storage capacitor means is transferred to the solenoid coil.

7. The apparatus of claim 1 wherein the acoustic sensor means includes a microphone sensor means and the computer processing means performs a calculation to determine a reverberation frequency of the sonic reverberation and the reverberation frequency is used to determine a sonic velocity.

8. The apparatus of claim 1 wherein the property information value is a modulus of elasticity, and calculation of the modulus of elasticity is of the form (constant) times (density) times (sonic velocity-squared).

9. The apparatus of claim 1 additionally including a pivot pin extending through a first stationary mounting plate and attached to a second rotatable mounting plate, a thrust bearing interposed between the first stationary mounting plate and the second rotatable mounting plate, a preload spring, a rotational stop and a spring means whereby the electric hammer is rigidly attached to the second rotatable mounting plate and both can rotate about a vertical axis of the pivot pin if the bimetallic armature is extended at a time when the wood lumber specimen is moving past the electric hammer, thereby allowing the wood lumber specimen to pass by the electric hammer without causing damage to the electric hammer, the bimetallic armature, the wood lumber specimen or to personnel or to property, and then to return to its original operating position by means of the rotational stop and the spring means.

10. The apparatus of claim 9 in which the thrust bearing is composed of ultra-high molecular weight polyethylene.

11. The apparatus of claim 1 in which the first linear bearing means is mounted in a bearing mount separately attached to the magnetic circuit means.

12. The apparatus of claim 11 in which the bearing mount contains the acoustic sensor means and the first linear bearing means.

13. The apparatus of claim 1 wherein the acoustic sensor means includes a plurality of acoustic sensors in contact with said wood lumber specimen at a corresponding multiplicity of distances from the first end of the wood lumber specimen whereby a sonic velocity is determined from the compressive stress wave at two or more of the acoustic sensors.

14. The apparatus of claim 13 wherein the acoustic sensor means includes a piezoelectric transducer means mounted inside a rotatable shell means and a coupling fluid whereby sonic energy from the sonic reverberation in the wood lumber specimen is conducted from the wood lumber specimen through the rotatable shell means, through the coupling fluid and to the piezoelectric transducer means.

15. The apparatus of claim 1 wherein the wood lumber density is determined from a weight measurement means, and a volume determining means.

16. The apparatus of claim 15 wherein the volume determining means includes manual input for length, width and thickness.

17. The apparatus of claim 15 wherein the volume determining means includes automatic sensor means for a value of one or more of length, width and thickness.

18. The apparatus of claim 15 wherein the weight measurement means includes an electronic load cell, a scale platform and a mechanical linkage means for transferring a force from a weight of the wood lumber specimen to the electronic load cell whereby only the weight caused forces in the vertical direction are directed to the electronic load cell and horizontal forces that result from friction and forces that result from movement of the wood lumber specimen along the scale platform are cancelled and whereby the weight caused force directed to the electronic load cell is independent of the location of the wood lumber specimen on the scale platform.

19. The apparatus of claim 18 further including a conveyor means with a multiplicity of lugs each lug including a roller attached thereto wherein the roller is rotatable about a horizontal axis parallel with the lengthwise direction of said wood lumber specimen whereby vertical friction force between the wood lumber specimen and the lug is reduced to a small value whereby the accuracy and repeatability of said weight measurement means is improved.

* * * * *